(12) United States Patent
Pacetti

(10) Patent No.: US 6,743,462 B1
(45) Date of Patent: Jun. 1, 2004

(54) APPARATUS AND METHOD FOR COATING IMPLANTABLE DEVICES

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/872,816

(22) Filed: May 31, 2001

(51) Int. Cl.⁷ .............................. A61L 27/00; B05D 1/02
(52) U.S. Cl. ..................... 427/2.24; 427/2.1; 427/2.25; 427/2.28; 427/2.3; 427/231; 427/232; 427/233; 427/234; 427/335; 427/236; 427/238; 427/239; 427/294; 427/296; 427/377; 427/378; 427/398.4; 427/421; 427/424; 427/425
(58) Field of Search ................................. 427/2.1, 2.24, 427/2.25, 2.28, 2.3, 231, 332, 233, 234–236, 238–239, 294, 296, 377–378, 398.4, 421, 424, 425

(56) References Cited

U.S. PATENT DOCUMENTS

| | | | | |
|---|---|---|---|---|
| 4,011,388 A | * | 3/1977 | Murphy et al. | 524/733 |
| 4,976,736 A | * | 12/1990 | White et al. | 424/423 |
| 5,358,740 A | * | 10/1994 | Bornside et al. | 118/52 |
| 5,643,580 A | * | 7/1997 | Subramaniam | 424/400 |
| 5,756,553 A | * | 5/1998 | Iguchi et al. | 424/425 |
| 5,897,911 A | | 4/1999 | Loeffler | 427/2.25 |
| 6,010,530 A | | 1/2000 | Goicoechea | 623/1 |
| 6,248,398 B1 | * | 6/2001 | Talieh et al. | 118/319 |
| 6,306,165 B1 | * | 10/2001 | Patnaik et al. | 427/2.25 |
| 6,358,556 B1 | * | 3/2002 | Ding et al. | 427/2.24 |
| 6,368,658 B1 | * | 4/2002 | Schwarz et al. | 427/2.15 |

* cited by examiner

Primary Examiner—Shrive P. Beck
Assistant Examiner—Jennifer Kolb Michener
(74) Attorney, Agent, or Firm—Squire, Sanders & Dempsey

(57) ABSTRACT

A method of forming a coating for an implantable medical device, such as a stent, is provided which includes applying a composition to the device in an environment having a selected pressure. An apparatus is also provided for coating the devices. The apparatus comprises a chamber for housing the device wherein the pressure of the chamber can be adjusted during the coating process.

10 Claims, 1 Drawing Sheet

APPARATUS AND METHOD FOR COATING IMPLANTABLE DEVICES

BACKGROUND OF THE INVENTION

1. Field of the Invention

This invention relates to an apparatus and method for coating implantable devices such as stents.

2. Description of the Background

Stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Mechanical intervention via stents has reduced the rate of restenosis; restenosis, however, is still a significant clinical problem. Accordingly, stents have been modified to perform not only as a mechanical scaffolding, but also to provide biological therapy.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

A common method of medicating a stent is by depositing a polymeric coating, impregnated with the therapeutic substance, on the surface of the stent. A polymer dissolved in a solvent is applied to the stent. A therapeutic substance can be dissolved or dispersed in the composition. The solvent is allowed to evaporate to form the coating. The application of the composition can be performed by spraying the composition on the stent or immersing the stent in the composition.

The solvents employed with the composition can be categorized as having a high vapor pressure or low vapor pressure. Non-volatile solvents evaporate very slowly from the composition causing coating defects such as inconsistency in the coating thickness and formation of "cob webs" or "pool webs" between the stent struts. A solution to this problem is to coat the stent at elevated temperatures to increase the evaporation rate of the solvent. However, not all drugs are stable at elevated temperatures. Volatile solvents have the tendency to evaporate very quickly from the composition resulting in a coating which has a powdered consistency and adheres poorly to the surface of the stent. Accordingly, what is needed is an apparatus and process for coating stents that does not suffer from the aforementioned drawbacks.

SUMMARY OF THE INVENTION accordance with one aspect of the invention, a method of forming a coating for an implantable medical device, such as a stent, is provided. The method comprises applying a composition to the stent in an environment having a pressure other than ambient pressure. For compositions including a non-volatile solvent, the pressure can be less that 760 torr; for compositions including a volatile solvent, the pressure can be greater than 760 torr. The composition can include a polymer, such as an ethylene vinyl alcohol copolymer dissolved in a solvent, such as dimethylacetamide. Optionally, a therapeutic substance can be added to the composition, such as actinomycin D, paclitaxel, docetaxel, or rapamycin. In accordance to one embodiment, the composition can be applied by spraying the composition on the stent. During the act of applying, the stent can be rotated and/or moved in a linear direction along the longitudinal axis of the stent. The stent can be a radially expandable stent, such as a balloon expandable or self-expandable type.

In accordance with another aspect of the invention, a method of forming a coating for a stent is provided, comprising positioning a stent in a chamber; applying a fluid to the stent; and adjusting the pressure of the chamber to increase or decrease the evaporation rate of the fluid.

In accordance with another aspect of the invention, an apparatus for coating implantable medical devices such as stents is provided. The apparatus includes a chamber for housing a stent and a pressure controller for adjusting the pressure of the chamber during the coating process to a pressure below or above 760 torr. In one embodiment, an applicator can be provided for spraying a composition at the stent. A support assembly holds the stents in the chamber and can be connected to a motor for providing rotational and/or translational motion to the stent. A temperature controller can also be provided for adjusting the temperature of the chamber.

DETAILED DESCRIPTION OF THE EMBODIMENTS

Embodiments of the Pressure Chamber

Figure 1:
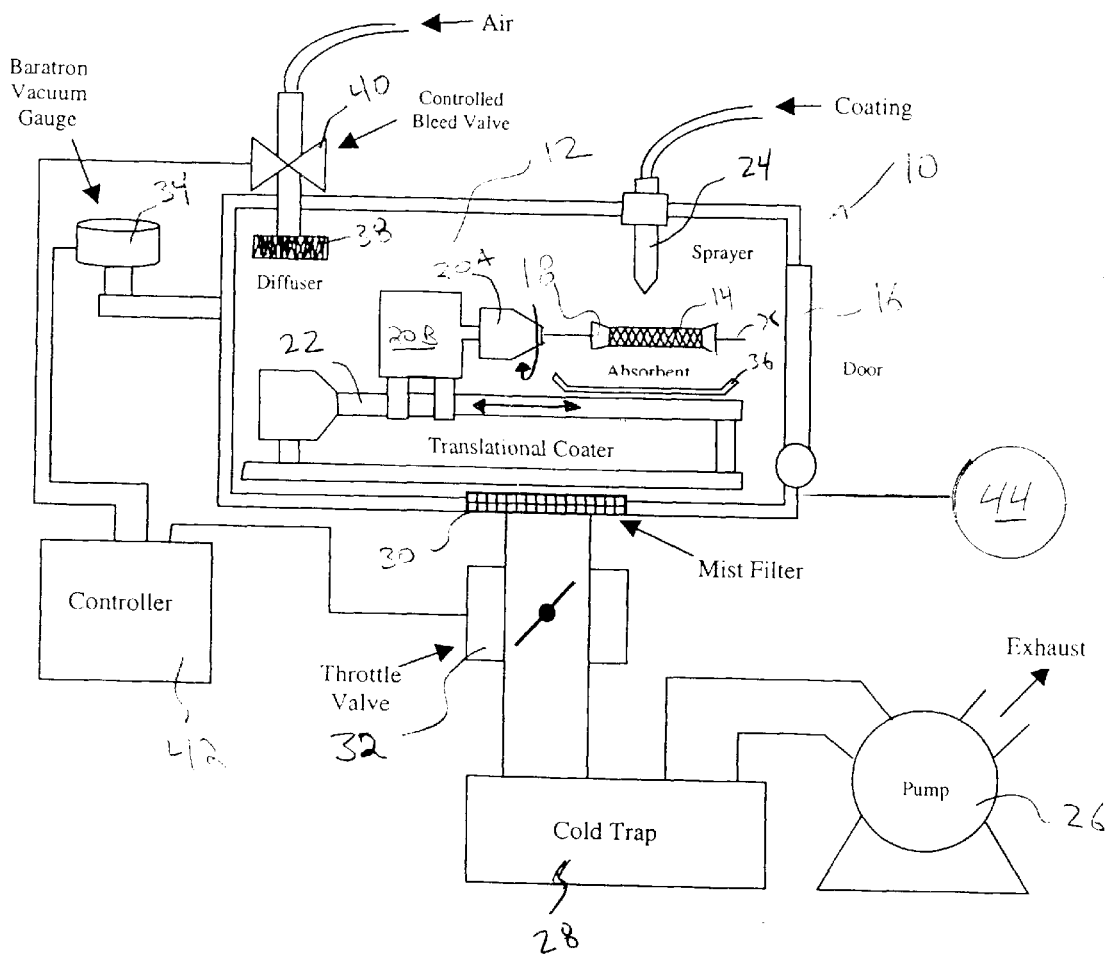
FIG. 1 illustrate a pressure chamber for forming a coating on a stent.

Referring to FIG. 1, there is illustrated a pressure chamber 10 defining a workspace 12 for depositing a composition on a stent 14 for forming a coating. A chamber opening (number omitted) can be provided for allowing a user to gain access into workspace 12. A hatch 16 can be placed over the chamber opening for tightly sealing the opening during the deposition process. The size of workspace 12 needs to be large enough so as to enclose a support assembly 18, such as a mandrel, for adequately supporting stent 14 during the coating process. Workspace 12 can be large enough so as to support any suitable number of support assemblies 18 and stents 14.

In one embodiment, support assembly 18 can be connected to a first motor assembly 20A for rotation of support assembly 18 along the central, longitudinal axis x of stent 14. A second motor assembly 20B can be additionally provided for translational movement of support assembly 18 in a linear direction, back and forth, along a railing 22. The rotational and translational motion of stent 14 during the application of the composition can result in a more uniform deposition of the coating.

An applicator 24, such as a spray valve, penetrates through the wall of pressure chamber 10 and is positioned in the vicinity of stent 14. Commercial applicators are available from Spray Systems Co., EFD International Inc., and Badger Air-Brush Co., one specific model of which is the EFD 780S spray device with VALVEMATE 7040 control system. To avoid spray rate alterations due to the pressure difference, applicator 24 can be placed entirely within pressure chamber 10. The nose of applicator 24 can be positioned at any suitable distance away from stent 14, for example at about 1 cm to about 10 cm. An operator should be capable of adjusting the distance depending on the particular circumstances of the deposition process. Applicator 24 is capable of applying the composition at a pressure of, for example, about 10 torr to about 1000 torr. In accordance with an alternative embodiment, support element 18 can be in a vertical position and applicator 24 spraying in a horizontal direction.

A pressure controller such as a pump 26 is in fluid communication with workspace 12 so as to create pressures below or above 760 torr (1 atm) in pressure chamber 10. In one embodiment, a cold trap 28 can be provided for preventing the solvent or condensation from penetrating into pump 26 should pump 26 be used to create a vacuum in pressure chamber 10. A filter 30, such as a mist filter, can also be provided to prevent droplets of coating composition from possibly reaching and damaging pump 26. Other components of pressure chamber 10 can include a throttle valve 32 for opening and closing the communication line to pump 26, a baratron vacuum gauge 34 for measuring the pressure in workspace 12 independent of the type and composition of the solvent vapor, and an absorbent 36 for capturing the bulk of the composition over-spray. Gas, such as air, can be pumped or bled into pressure chamber 10 for creating a convection flow inside pressure chamber 10, to actively scavenge the solvent vapor from workspace 12 and out through pump 26 so as to prevent solvent vapor build-up. A diffuser 38 can be used to diffuse or "spread out" the flow of gas so as to minimize disturbance of the spraying process. A bleed valve 40 can be used for adjusting the flow rate of gas through diffuser 38. In addition to rapidly removing the solvent vapor from pressure chamber 10, bleed valve 40 can also be used to control the chamber pressure by working in concert with throttle valve 32.

Pressure chamber 10 can also be connected to a heating and/or cooling source 44 so as to control the temperature of workspace 12. A cooler deposition environment, such as temperatures of less than 50° C. may be preferred depending on the chemical stability of the therapeutic substance and the type solvent used. In lieu of providing and external heating source, an internal component, such as heating and/or cooling coils, can be provided.

Method of Applying the Composition

To form a coating on a surface of stent 14, the surface of stent 14 should be clean and free from contaminants that may be introduced during manufacturing. However, the surface of stent 14 requires no particular surface treatment to retain the applied coating. Stent 14 is mounted on mandrel 18 and the composition is sprayed via applicator 24 at a pressure of, for example between 10 to 1000 torr. During the spraying of the composition, stent can be rotated at about 1 to about 120 rotations per minute. Stent 14 can also be moved in a linear direction at speed of about 1 to about 20 cm/sec. The temperature of chamber 10 should be maintained at a temperature that does not adversely affect the therapeutic substance or the coating process—for example at about 20° C. to about 50° C.

For a solvent having a low vapor pressure (e.g., below 30 torr at the temperature of application), or in other words non-volatile substances, the solvent evaporates very slowly from the composition, leading to irregularities in the coating thickness and "cob webs" or "pool webs" between the stent struts. Accordingly, compositions have been applied in short bursts, interrupted by the drying of the composition between each application step to minimize coating defects. Reducing the pressure of chamber 10 below ambient pressure during the coating process allows the solvent to evaporate more rapidly. Rapid evaporation of the solvent allows the composition to be applied continuously for depositing a coating of a suitable thickness or weight while minimizing coating defects such as "pool webs." The pressure employed in pressure camber 10 depends on the type of solvent employed. Table 1 is an exemplary list of non-volatile solvents and the suitable range of pressure which can be used in the process of the present invention:

TABLE 1

| Solvent | Exemplary Pressure Ranges torr @ 20° C. |
|---|---|
| Dimethylsulfoxide | 0.8–<760 |
| Dimethlacetamide | 0.9–<760 |
| Dimethylformamide | 5.4–<760 |

For a solvent having a high vapor pressure (e.g., above 30 torr at the temperature of application), or in other words volatile solvents, the solvent evaporates extremely rapidly from the composition, leading to difficulties in the application of the composition to the stent. Application of such compositions often lead to coatings having powdered consistency and poor adhesion of the coating to the surface of the stent. Increasing the pressure in pressure chamber 10 above ambient pressure causes the solvent to evaporate more slowly leading to a coating with a smoother surface, more uniform composition, and better adhesion. Table 2 is an exemplary list of volatile solvents and the suitable range of pressure which can be used in the process of the present invention:

TABLE 2

| Solvent | Exemplary Pressure Ranges torr @ 20° C. |
|---|---|
| Toluene | >760–2000 |
| n-propanol | >760–3400 |
| Acetone | >760–9000 |

The Composition

The embodiments of the composition can be prepared by conventional methods wherein all components are combined, then blended. More particularly, in accordance to one embodiment, a predetermined amount of a polymer or combination of polymers can be added to a predetermined amount of a solvent or a combination of solvents. If necessary, heating, stirring and/or mixing can be employed to effect dissolution of the polymer(s) into the solvent(s)— for example in an 80° C. water bath for two hours. A therapeutic substance can be also added to the composition. The therapeutic substance should be in true solution or saturated in the blended composition. If the therapeutic substance is not completely soluble in the composition, operations including mixing, stirring, and/or agitation can be employed to effect homogeneity of the residues. The therapeutic substance may be added so that dispersion is in fine particles. The mixing of the therapeutic substance can be conducted at ambient pressure and at room temperature.

The polymer or combination of polymers chosen must be biocompatible and minimize irritation to the vessel wall when the device is implanted. The polymer may be either a biostable or a bioabsorbable polymer. Bioabsorbable polymers that could be used include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly (ether-esters) (e.g. PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used. Other polymers include polyolefins, polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose, cellulose acetate; cellulose butyrate; cellulose acetate butyrate; cellophane; cellulose nitrate; cellulose propionate; cellulose ethers; and carboxymethyl cellulose. Ethylene vinyl alcohol is functionally a very suitable choice of polymer. The copolymer possesses good adhesive qualities to the surface of a stent, particularly stainless steel surfaces, and has illustrated the ability to expand with a stent without any significant detachment of the copolymer from the surface of the stent. The copolymer, moreover, allows for good control capabilities over the release rate of the therapeutic substance.

Representative examples of solvents include chloroform, acetone, water (buffered saline), dimethylsulfoxide (DMSO), propylene glycol methyl ether (PM,) isopropylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, acetone, 2-butanone, cyclohexanone, dioxane, methylene chloride, carbon tetrachloride, tetrachlroro ethylene, tetrachloro ethane, chlorobenzene, 1,1,1-trichloroethane, formamide, and combination there of. The solvent should be capable of placing the selected polymer into dissolution at the selected concentration and should not adversely react with the therapeutic substance.

The therapeutic substance can include any agent capable of exerting a therapeutic or prophylactic effect in the practice of the present invention such as inhibition of migration and/or proliferation of smooth muscle cells. The agent can also be for enhancing wound healing in a vascular site and improving the structural and elastic properties of the vascular site. Examples of agents include antiproliferative substances as well as antineoplastic, antiinflammatory, antiplatelet, anticoagulant, antifibrin, antithrombin, antimitotic, antibiotic, antioxidant, and combinations thereof. One suitable example of an antiproliferative substance includes actinomycin D—synonyms of which include dactinomycin, actinomycin IV, actinomycin $I_1$ actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, rapamycin, and dexamethasone.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Stent is broadly intended to include self-expandable stents, balloon-expandable stents, and stent-grafts. One of ordinary skill in the art, however, understands that other medical devices on which a polymer can be coated can be used with the practice of the present invention, such as grafts (e.g., aortic grafts), endocardial leads, valves, and alike. The underlying structure of the device can be virtually any design. Stents are typically defined by tubular body having a plurality of bands or cylindrical elements interconnected by connecting elements. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum.

"MP20N" consists of 50% cobalt, 20% nickel, 20% chromium, and 10% molybdenum. Devices made from bioabsorbable or biostable polymers could also be used with the blended composition.

While particular embodiments of the present invention have been shown and described, it will be obvious to those skilled in the art that changes and modifications can be made without departing from the embodiments this invention in its broader aspects and, therefore, the appended claims are to encompass within their scope all such changes and modifications as fall within the true spirit and scope of the embodiments this invention.

What is claimed is:

1. A method of forming a coating for an implantable medical device, comprising:
   a) inserting the device into a chamber;
   b) adjusting the pressure of the chamber to other than ambient pressure;
   c) applying a composition comprising a solvent to the implantable device while the device is disposed in an environment having a pressure other than ambient pressure
      i) if the composition includes a non-volatile solvent, then other than ambient pressure is less than 760 torr; and alternatively,
      ii) if the composition includes a volatile solvent, then other than ambient pressure is greater than 760 torr.

2. The method of claim 1, wherein the composition comprises a polymer dissolved in a solvent and optionally a therapeutic substance added thereto.

3. The method of claim 2, wherein the therapeutic substance is actinomycin D, paclitaxel, docetaxel, or rapamycin.

4. The method of claim 2, wherein the polymer is an ethylene vinyl alcohol copolymer.

5. The method of claim 1, wherein the act of applying comprises spraying the composition on the implantable device.

6. The method of claim 1, wherein the implantable device is a stent and the act of applying comprises spraying the composition while rotating the stent about the longitudinal axis of the stent.

7. The method of claim 1, wherein the implantable device is a stent and the act of applying comprises spraying the composition while moving the stent in a linear direction along the longitudinal axis of the stent.

8. The method of claim 1, wherein the implantable device comprises a radially expandable stent, graft, or a stent-graft.

9. The method of claim 8 wherein the composition includes a therapeutic substance and wherein the temperature of the chamber is adjusted to a temperature that does not adversely affect the therapeutic substance.

10. The method of claim 8 wherein the composition includes a polymer dissolved in the solvent.

* * * * *